United States Patent [19]
McNally et al.

[11] Patent Number: 6,149,617
[45] Date of Patent: Nov. 21, 2000

[54] TENNIS ELBOW BAND AND METHOD

[75] Inventors: William L. McNally, Weston; Rhonda M. Falk, Tamarac, both of Fla.

[73] Assignee: FLA Orthopedics, Inc., Miramar, Fla.

[21] Appl. No.: 09/358,966

[22] Filed: Jul. 22, 1999

Related U.S. Application Data

[62] Division of application No. 09/024,815, Feb. 17, 1998, Pat. No. 5,971,947.

[51] Int. Cl.$^7$ ............................... A61F 5/00; A61F 13/00
[52] U.S. Cl. ................... 602/62; 602/2; 602/20; 607/112
[58] Field of Search ................... 602/14, 20, 21, 602/23, 26, 60, 61, 62, 63, 79, 13; 128/DIG. 15, 876, 877, 878, 882; 2/16, 162, 170

[56] References Cited

U.S. PATENT DOCUMENTS

| | | |
|---|---|---|
| 3,623,485 | 11/1971 | Price . |
| 3,780,537 | 12/1973 | Spencer ..................................... 62/530 |
| 4,381,025 | 4/1983 | Schooley .................................. 150/2.4 |
| 4,628,918 | 12/1986 | Johnson, Jr. . |
| 5,152,302 | 10/1992 | Fareed ..................................... 128/878 |
| 5,165,402 | 11/1992 | McCoy . |
| 5,591,221 | 1/1997 | Owens ..................................... 607/114 |
| 5,593,769 | 1/1997 | Wolf et al. .............................. 428/286 |

*Primary Examiner*—Kim M. Lee
*Attorney, Agent, or Firm*—Jack E. Dominik

[57] ABSTRACT

A tennis elbow band with a body having an end tab at one end, a strap portion, a thermal packet pocket secured to the strap at a position remote from the end tab, and a combination leverage loop and shield at the far end remote from the end tab to give mechanical assistance in tightening the band prior to securement by the end tab overlapping a portion of the strap. The thermal packet pocket is positioned immediately at the leverage loop at the end of the strap and removably receives a thermal packet. The method of the present invention is directed primarily to determining the condition of the patient, and thereafter removing the thermal packet and conditioning it to the desired temperature of either cold or heat and thereafter inserting the same into the band pocket. Once inserted into the band, the tab is passed through the leverage loop which causes the shield to engage the outer surface of the limb and protect from pinching which might otherwise occur as the strap wraps around the leverage loop and the end tab is thereafter secured on the body portion midway between the end tab and the pocket.

3 Claims, 2 Drawing Sheets

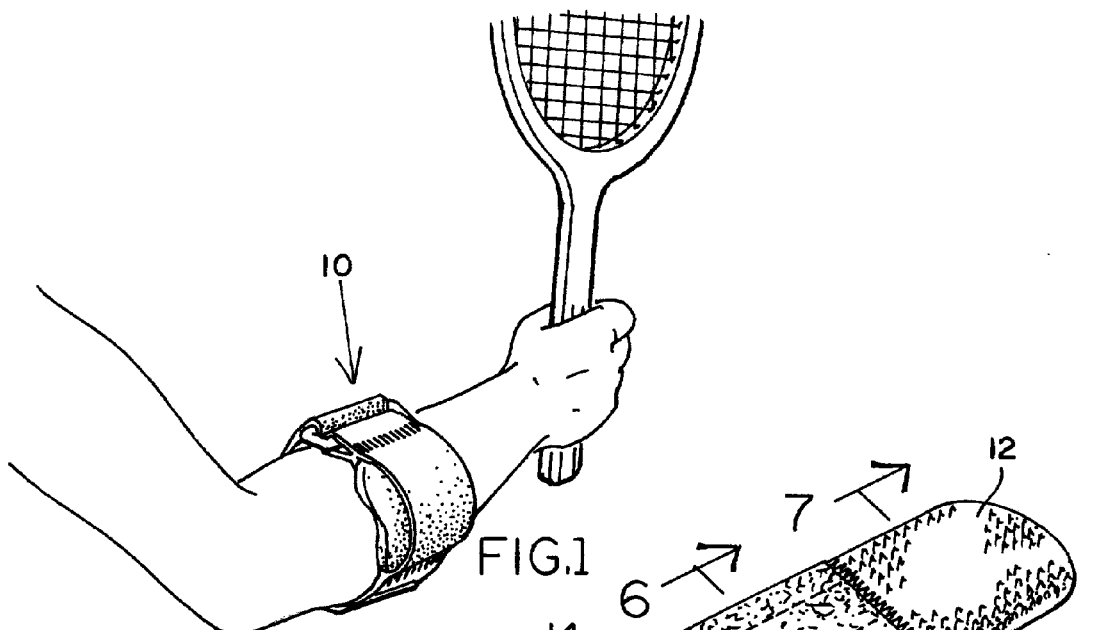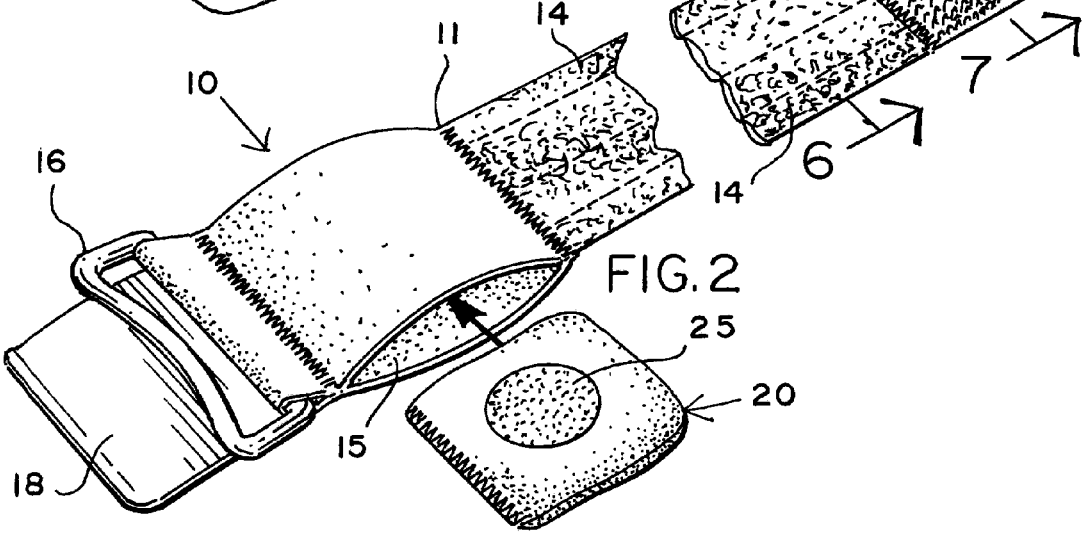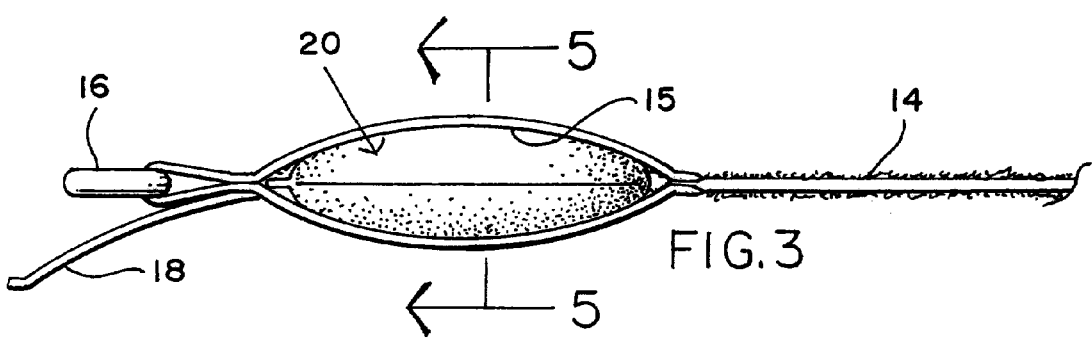

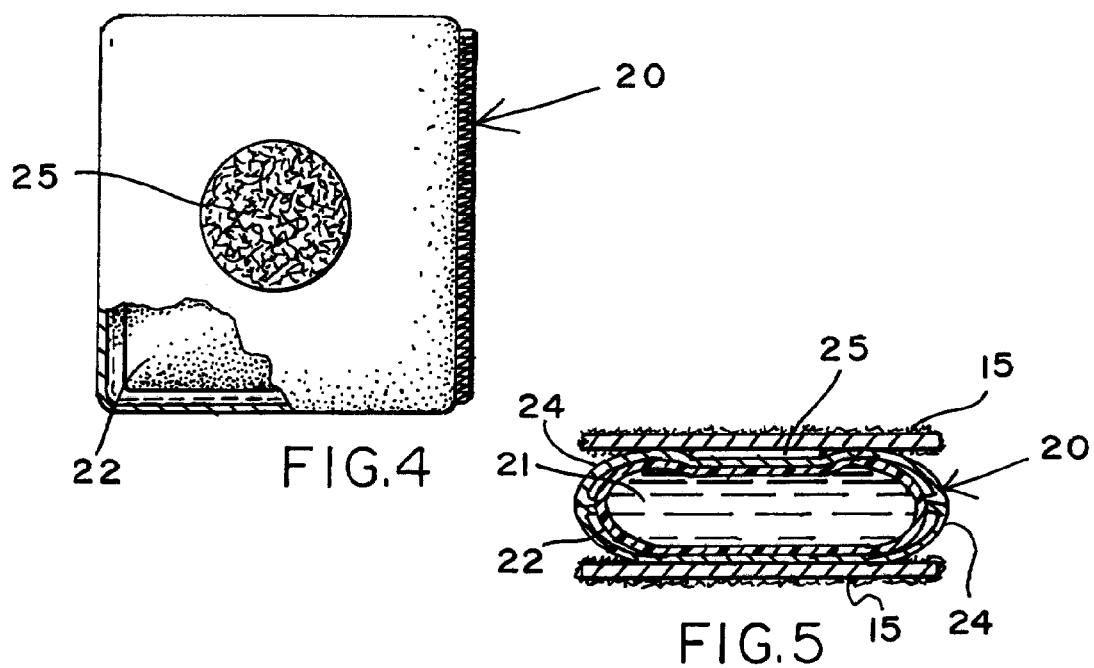
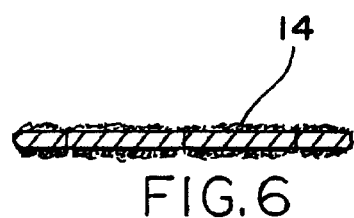
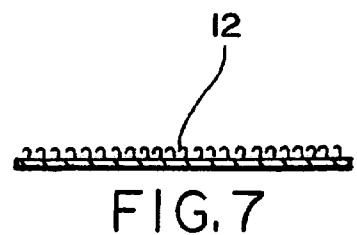

TENNIS ELBOW BAND AND METHOD

This Application is a Divisional of application Ser. No. 09/024,815, filed Feb. 17, 1998 now U.S. Pat. No. 5,971,947.

FIELD OF THE INVENTION

The present invention relates to the general field of orthopedic devices, and more particularly a band which ideally is secured around the forearm to reduce problems with "tennis elbow" and other muscular strain attributable to unusual conditions of use of the forearm.

BACKGROUND OF THE INVENTION

The prior art is exemplified by an armband manufactured and sold under the trademark AIRCAST® and a related device disclosed in U.S. Pat. No. 4,628,918. The device of the subject patent relies upon an inflatable bladder. Also employed, however, is a unit having a non inflatable bladder. The deficiencies of the subject construction are numerous. They do not readily permit application of hot or cold since a bag of air is basically an insulator at both extremes of temperature. Another relevant patent is U.S. Pat. No. 5,295,951 which contains an adjustable pressure point. Again, it fails to address the thermal properties which can be important. U.S. Pat. No. 5,152,302 by the same inventor involves 2 opposing means for applying transaxial compression. U.S. Pat. No. 4,913,755 references a resilient support with a gel filled cushion pad to apply against the ankle. A vacuum chamber is involved in the process and complex sealing is employed. Another related patent is U.S. Pat. No. 5,027,801 again utilizing an orthopedic gel pad, but even requiring stiff supports. What the prior art has failed to address is the desirability for being able to precondition the point of pressure as to temperature. In orthopedic applications, normally for the first 72 hours after injury, cold packs are employed. After those 72 hours, quite often a heated pad is to be applied to assist in the healing or curative process.

SUMMARY OF THE INVENTION

The present invention is directed to a tennis elbow band with a body having an end tab at one end, a strap portion, a thermal packet pocket secured to the strap at a position remote from the end tab, and a combination leverage loop and shield at the far end remote from the end tab to give mechanical assistance in tightening the band prior to securement by the end tab overlapping a portion of the strap. The thermal packet pocket is positioned immediately at the leverage loop at the end of the strap and removably receives a thermal packet. The thermal packet can be placed in a freezer, or a microwave, and quickly brought to a temperature where the therapeutic effect can be appreciated by the user wearing the tennis elbow band while applying heat under pressure, or cold under pressure to the point of sensitivity, when there is incipient damage, or even damage during the healing process. Moreover, the same can be worn at a neutral temperature to compress the forearm while at the same time not inhibiting desirable circulation. Thus, the band can be directed against flexure muscles, or radial extensor to achieve the compression desired by the user. The method of the present invention is directed primarily to determining the condition of the patient, and thereafter removing the thermal packet and conditioning it to the desired temperature of either cold or heat and thereafter inserting the same into the band pocket. Once the thermal packet is inserted into the pocket on the band, the band is removably secured, but firmly engaged around the forearm of the user to apply the pressure of the thermal packet to that portion of the limb requiring therapy, and the, the tab is passed through the leverage loop which causes the shield to engage the outer surface of the limb and protect from pinching which might otherwise occur as the strap wraps around the leverage loop and the end tab is thereafter secured on the body portion midway between the end tab and the pocket.

In view of the foregoing it is a principal object of the present invention to provide a tennis elbow band which can pre-selectively be applied at a pressure point to transfer heat, cold, or neutral temperature, plus pressure to that portion of the limb being treated.

A related object of the present invention is to provide a tennis elbow band with the thermal properties desired which is inherently cost effective when compared to other tennis elbow bands.

Yet another more specific object of the present invention is to provide a tennis elbow band with a compressible gel like material which is removable for purposes of heat or cold applications, and which band, after removal of the thermal packet, can be cleaned easily by the normal washing machine, in a washbowl, or wherever a source of fluid is available.

DESCRIPTION OF ILLUSTRATIVE DRAWINGS

Further objects and advantages of the present invention will become apparent as the following description proceeds, taken in conjunction with the accompanying drawings in which:

FIG. 1 illustrates the forearm of an athlete grasping a handle with the subject illustrative tennis elbow band secured along the forearm adjacent the elbow;

FIG. 2 is a plan partially broken view of the entire tennis elbow strap;

FIG. 3 is a side view of the thermal packet and the related buckles;

FIG. 4 is an enlarged illustrative broken view of the thermal packet and its immediate exterior absorbent cover;

FIG. 5 is a transverse sectional view of the thermal packet insert taken along section line 5—5 of FIG. 3;

FIG. 6 is a transverse sectional view taken of the strap along section line 6—6 of FIG. 2; and FIG. 7 is yet another transverse sectional view of the tab taken along section line 7—7 of FIG. 2.

DESCRIPTION OF THE PREFERRED EMBODIMENT

Set forth in the description of drawings above, FIG. 1 shows the illustrative tennis elbow band 10 applied around the forearm of the user. Readily visible is the upper arm, the elbow, the forearm, the wrist, and the hand of the user. A handle is shown for illustrative purposes which could be a tennis racket, a baseball bat, or a carpenter's hammer. While the name of the product "Tennis Elbow" band would imply that its usage is limited to the impact received by a tennis player, this is not the case. The band has applicability wherever the flexor muscles of the forearm require support and more particularly the application of a thermal treatment simultaneously with the support function.

Turning now to FIG. 2, it will be seen that the entire strap 10 is essentially elongate having a body portion 11 which has a securing tab 12, a strap portion 14 comprises the major length of the band 10. At the end of the strap 14 remote from the tab 12 a pocket 15 is provided to removably receive and retain the thermal packet 20.

A leverage loop 16 is at the very remote end of the strap 14 and defines a loop with a narrow center portion through which the tab 12 can be inserted and reversibly folded. A shield 18 is provided to engage the forearm underneath the leverage loop 16 to thereby shield the skin of the arm from impact or pinching by the leverage loop, and the reversely folded strap 14 when in the locked configuration.

As shown, particularly in FIGS. 4 and 5, the thermal insert 20 includes a gel base 21 held interiorly of a bag 22. More specifically, the desired product for encapsulating the gel 21 is a polyurethane foam backed releasable hook or loop compatible laminate bag 22 which, during the laminating process, creates a moisture barrier in the encapsulating the gel. Similarly, the barrier permits a gentler application of heat or cold to the area designated for treatment. Thus, the gel packet 20 can be positioned in a microwave, and yet when heated, can be handled with bare hand. Similarly, when placed in a freezer, it will not harden but remain sufficiently pliable to the hand when removed from the freezer and positioned in the strap for subsequent application by the user.

The particular gel is Elasto-Gel™ Therapy Products, from Southwest Technologies, Inc. It is made of a tough, flexible gel covered with a four way stretch material, which allows maximum conformity, heat transfer and comfort. A single product serves both hot or cold applications.

COLD: The wrap remains soft and flexible at temperatures as low as 20° F. The cold wrap will usually numb the treated area within 5 minutes without the severe shock and pain experienced with ice or ice water treatments. The product will remain cold for 20–30 minutes. When storing Elasto-Gel™ in a freezer, the product should always be kept in a reclosable plastic bag to keep gel from absorbing excessive moisture. DO NOT GET PRODUCT WET.

HOT: Moist heat quickly penetrates muscles and joints when applied. The product can be heated in a Microwave. Extreme caution is recommended when using Elasto-Gel™ because the gel does provide moist heat, the product gradually gets warmer after being applied to the body. It is recommended that the surface feels warm, not hot, before applying to the patient. If the product feels hot on the surface it can burn the patient. Elasto-Gel™ generates steam heat which becomes trapped against the body upon application. Elasto-Gel™ will not leak if punctured and is safe for direct contact to open wounds. Due to the nature of the glycerine base gel, no rehydration is necessary, even after many uses of heat therapy.

Finally, a thermal wrap 24 is applied around the bag 22 to prevent moisture from penetrating the gel base itself, since the slightest amount of moisture can cause this particular gel to go into "shock" and become harden and/or gravel like. Also, it will be seen that a locking spot 25 is provided on the gel insert 20 to removably secure the same interiorly of the pocket 15.

The releaseable securing means interiorly of the pocket applied to the exterior portion of the strap 14 are commonly known as Velcro® hooks and loops. Opposed location of such hooks and loops are employed for securing the thermal packet 20 into the pocket 15, and similarly for securing one end of the tab 12 to the strap 14 after the strap has been passed through the leverage loop 16 and the double fold portion of the strap 14 wraps itself around the shield 18 securing the shield 18 against the forearm. Once the desired amount of compression is attained, the tab 12 is secured against the strap 14. The thermal packet 20 is secured in place after the tennis elbow band 10 is in place or prior thereto. The prior insertion is preferred since it pre-disposes the gel pack 20 interiorly of the pocket 15 in a relaxed mode, and squeezing and pushing are thereby minimized. The overlapping layered configuration of pocket 15, insert 20, skin 22, and insulation 24 are all shown in the sectional view in FIG. 5. Similarly the strap and its loop hook arrangements are shown in FIG. 6, with FIG. 7 illustrating the loop hook relationship at the end of tab 12.

The Materials:

While the materials are not considered essential to the invention, the same are set forth in order to teach one skilled in the art as to the best mode known to the Applicant for practicing the invention:

TENNIS ELBOW BAND AND METHOD MATERIALS

| | Materials | Vendor | Specs | Properties |
|---|---|---|---|---|
| Strap | 2" wide double faced loop | Velcro ® USA | Medium cycle life loop compatible material | Plush but durable hook compatible material |
| Buckle | 2" wide high gloss buckle | Aurora Plastics | Polypropylene | Ultra strong buckle with high gloss finish for reduction friction |
| Tension Loop | 2" wide high gloss tension loop | Aurora Plastics | Poly propylene | Ultra strong guide with high gloss finish for reduced friction, also reduces bunching |
| Pocket | 2" wide velstretch loop material | Velcro ® USA | Medium cycle life stretchable loop compatible material | Comfortable, yet resilient hook compatible material |
| Gel | 2"½ x 2" x 36" block of visco-elastic gel | Viscolas Co. | Currently being tested by NAMSA labs. | Provides therapeutic heat and cold, for 30 minutes plus, while maintaining its supple feel, |

-continued

TENNIS ELBOW BAND AND METHOD MATERIALS

| Materials | | Vendor | Specs | Properties |
|---|---|---|---|---|
| Thermal Packet Cover | 3" wide ⅛ oster loop material | Quimat Co. | Foam backed loop compatible laminate | and focused pressures Comfortable foam cover protects thermal packet from moisture while improving comfort, and enhancing the thermal properties of the thermal packet |

The Method:

The method of the present invention is directed primarily to determining the therapy required for the user as to heat, cold, or neutral. Thereafter, the insert 20 is either placed in a freezer for a period of time, a cooler, or a heating environment. With the preferred gel set forth above, heating in a microwave in a matter of seconds can be readily achieved. Chilling in a freezer requires 15 minutes to an hour depending upon the temperature desired.

Once the temperature therapy has been determined the packet is ideally secured in the pocket 15 of the tennis elbow strap 10, and positioned in pressure engagement with the forearm and the tab 12 secured to the body strap 14.

It will be understood that various changes in the details, materials and arrangements of parts, or method which have been herein described and illustrated in order to explain the nature of the invention, may be made by those skilled in the art within the principle and scope of the invention as expressed in the appended claims.

What is claimed is:

1. The method of treating the tennis elbow symptom, comprising the steps of:

providing a tennis elbow band comprising in combination: an elongate body portion; an end tab forming one end of said elongate body portion having at least one surface covered with releasable securing material, said elongate body having a strap portion comprising a main intermediate portion of the tennis elbow band leading to a position remote from the end tab; a pocket formed at an end of the strap portion for receiving a thermal packet having a gel center, said pocket having releasable securing means interior thereof for securing the thermal packet once received therein, said thermal packet being enclosed by a polyurethane foam backed hook or loop compatible laminate, wherein the laminate creates a moisture resistant encasement for the packet; a leverage loop positioned at one side of the pocket remote from the portion of the pocket engaging the strap portion, and means on the strap for releasable engagement to the end tab after the strap has been pulled to hold the packet in thermal contact against the limb of a user;

determining the condition of the user;

determining the temperature therapy to be applied to the user;

chilling or heating the thermal packet depending upon which temperature is desired;

subsequently inserting the thermal packet into the pocket of the strap; and thereafter removably securing, but firmly engaging, the tennis elbow strap around the forearm of the user applying the pressure of the thermal packet to that portion of the limb requiring therapy.

2. The method of treating the tennis elbow symptom, comprising the steps of:

providing a tennis elbow band comprising in combination: an elongate body portion; an end tab forming one end of said elongate body portion having at least one surface covered with releasable securing material, said elongate body having a strap portion comprising a main intermediate portion of the tennis elbow band leading to a position remote from the end tab; a pocket formed at an end of the strap portion for receiving a thermal packet having a gel center which when cooled will remain cool for twenty minutes, said thermal packet being enclosed by a polyurethane foam backed releasable compatible laminate, wherein the laminate creates a moisture resistant encasement for packet; a leverage loop positioned at one side of the pocket remote from the portion of the pocket engaging the strap portion, and means on the strap for releasable engagement to the end tab;

determining the condition of the user;

determining the temperature therapy to be applied to the user;

chilling the thermal packet to a desired temperature;

subsequently inserting the thermal packet into the pocket of the strap; and thereafter removably securing, but firmly engaging, the tennis elbow strap around the forearm of the user applying the pressure of the thermal packet to that portion of the limb requiring therapy.

3. The method of treating the tennis elbow symptom, comprising the steps of:

providing a tennis elbow band comprising in combination: an elongate body portion; an end tab forming one end of said elongate body portion having at least one surface covered with releasable securing material, said elongate body having a strap portion comprising a main intermediate portion of the tennis elbow band leading to a position remote from the end tab; a pocket formed at an end of the strap portion for receiving a thermal packet, said thermal packet having a gel in its center, said thermal packet being enclosed by a polyurethane foam backed releasable compatible laminate, wherein the laminate creates a moisture resistant encasement for packet; a leverage loop positioned at one side of the pocket remote from the portion of the pocket engaging the strap portion, and means on the strap for releasable engagement to the end tab;

determining the condition of the user;

determining the temperature therapy to be applied to the user;

chilling or heating the thermal packet depending upon which temperature is dictated;

subsequently inserting the packet into the pocket of the strap; and thereafter removably securing, but firmly engaging, the tennis elbow strap around the forearm of the user applying the pressure of the thermal packet to that portion of the limb requiring therapy.

* * * * *